US008524674B2

(12) United States Patent
Khavinson et al.

(10) Patent No.: US 8,524,674 B2
(45) Date of Patent: Sep. 3, 2013

(54) METHOD OF IMPROVING THE CONDITIONED REFLEX HABIT, THE MUSCLE TONUS, OR THE MOTION COORDINATION OF A PATIENT AFTER SUFFERING TRAUMA TO THE BRAIN CORTEX

(75) Inventors: Vladimir Khatskelevich Khavinson, St. Petersburg (RU); Evgeny Iosifovich Grigoriev, St. Petersburg (RU); Vladimir Victorovich Malinin, St. Petersburg (RU); Galina Anatolievna Ryzhak, St. Petersburg (RU)

(73) Assignee: Obschestvo S Ogranichennoi Otvetstvennostyu "Sia Peptides", St. Petersburg (RU)

( * ) Notice: Subject to any disclaimer, the term of this patent is extended or adjusted under 35 U.S.C. 154(b) by 0 days.

(21) Appl. No.: 13/586,312

(22) Filed: Aug. 15, 2012

(65) Prior Publication Data
US 2012/0309688 A1 Dec. 6, 2012

Related U.S. Application Data

(63) Continuation of application No. 12/298,420, filed as application No. PCT/RU2006/000653 on Dec. 4, 2006, now abandoned.

(30) Foreign Application Priority Data

May 30, 2006 (RU) .............................. 2006118494

(51) Int. Cl.
*A61K 38/00* (2006.01)
(52) U.S. Cl.
USPC .......... 514/21.9; 514/1.1; 514/17.7; 530/300; 530/333
(58) Field of Classification Search
None
See application file for complete search history.

(56) References Cited

U.S. PATENT DOCUMENTS

| | | | |
|---|---|---|---|
| 6,727,227 B1 | 4/2004 | Khavinson et al. | |
| 7,189,701 B1 | 3/2007 | Khavinson et al. | |
| 7,851,449 B2 | 12/2010 | Khavinson et al. | |
| 8,057,810 B2 | 11/2011 | Khavinson et al. | |
| 8,071,556 B2 | 12/2011 | Khavinson et al. | |
| 2004/0102370 A1 | 5/2004 | Saffell | |
| 2004/0266991 A1 | 12/2004 | Liesi | |

FOREIGN PATENT DOCUMENTS

| | | |
|---|---|---|
| WO | WO 98/09985 | 3/1998 |
| WO | WO 01/29067 A1 | 4/2001 |
| WO | WO 01/47950 A | 7/2001 |
| WO | WO 02/30955 A2 | 4/2002 |
| WO | WO 02/34776 A2 | 5/2002 |
| WO | WO 2005/056580 A | 6/2005 |
| WO | WO 2006/001728 A | 1/2006 |
| WO | WO 2007/136294 A1 | 11/2007 |
| WO | WO 2007/136295 A2 | 11/2007 |
| WO | WO 2007/139435 A1 | 12/2007 |

OTHER PUBLICATIONS

Hartke et al 2011 RIC Life Center.*
Ridley 2011.*
Abiko, Takashi, et al., "Characterization of an Acidic Tripeptide in Neutotoxic Dialysate," *Chemical & Pharmaceutical Bulletin*, vol. 28, No. 5, May 1980, pp. 1629-1633.
Barabanova, S.V. et al., "[Parallel Analysis of C-Fos Protein and Interleukin-2 Expression in Hypothalmic Cells Under Different Influence]" Feb. 2007, pp. 150-160, vol. 92, No. 2, Rossi §SKII Fiziologicheski § Zhurnal Imeni I.M. Sechenova, Rossi §Skaia Akademiia Nauk.
Brasnjevic, Ivona, et al., "Delivery of peptide and protein drugs over the blood-brain barrier," *Progress in Neurobiology*, vol. 87, pp. 212-251 (2009).
Deumens, Ronald, et al., "Regeneration of descending axon tracts after spinal cord injury," *Progress in Neurobiology*, vol. 77, pp. 57-89 (2005).
Horner, Philip J., et al., "Regenerating the damaged central nervous system," *Nature*, vol. 407, pp. 963-970 (Oct. 26, 2000).
Illis, LS, "Central nervous system regeneration does not occur," *Spinal Cord*, pp. 1-5 (2011).
Khavinson, V Kh. et al., "Mechanisms Underlaying Geroprotective Effects of Peptides" *Bulletin of Experimental Biology and Medicine*, Jan. 2002, pp. 1-5, vol. 133, No. 1, Consultants Bureau, New York, NY.
Korkushko O. V. et al., "Geroprotective Effect of Epithalamine (Pineal Gland Peptide Preparation) in Elderly Subjects with Accelerated Aging" *Bulletin of Experimental Biology and Medicine*, Sep. 1, 2006, pp. 356-359, vol. 142, No. 3, Kluwer Academic Publishers, NE.
Malavolta, Luciana, et al., "Peptides: Important tools for the treatment of central nervous system disorders," *Neuropeptides*, vol. 45, pp. 309-316 (2011).
Mileusnic, R. et al., "The Peptide Sequence Arg-Glu-Arg, Present in the Amyloid Precursor Protein, Protects Against Memory Loss Caused by Abeta and Acts as a Cognitive Enhancer" *European Journal of Neuroscience*, Apr. 2004, pp. 1933-1938, vol. 19, No. 7, Oxford University Press, Great Britain.
Ruiz-Alcaraz, Antonio J., et al., "Gonadins, a novel family of glutamyl-tripeptide amides present in the testis with activity in the hypophyseal-gonadal axis," *Regulatory Peptides*, vol. 129, 2005, pp. 93-101.
Sibarov, D.A. et al., "Epitalon Influences Pineal Secretion in Stress-Exposed Rats in the Daytime" *Neuroendocrinology Letters*, 2002, pp. 452-454, vol. 23, No. 5-6, Sweden.
Slootstra, Jerry W., et al., "Structural aspects of antibody-antigen interaction revealed through small random peptide libraries," *Molecular Diversity*, vol. 1, pp. 87-96 (1995).
Taylor, Eve M., et al., "Designing Stable Blood-Brain Permeable Prosaptide Peptides for Treatment of Central Nervous System Neurodegeneration," *The Journal of Pharmacology and Experimental Therapeutics*, vol. 293, No. 2, pp. 403-409 (2000).
Wang Chao et al., "The Synthesis and Immunosuppressive Activities of Steroid-urotoxin Linkers" *Bioorganic & Medicinal Chemistry*, Aug. 15, 2004, pp. 4403-4421, vol. 12, No. 16.
Pardridge, William M., "Blood-Brain Barrier Drug Targeting: The Future of Brain Drug Development," *Molecular Interventions*, v. 3, 90-104 (2003).

\* cited by examiner

*Primary Examiner* — Cecilia J Tsang
*Assistant Examiner* — Li Lee
(74) *Attorney, Agent, or Firm* — Leydig, Voit & Mayer, Ltd.

(57) ABSTRACT

Disclosed is a method of improving the conditioned reflex habit, the muscle tonus, or the motion coordination of a patient after suffering trauma to the brain cortex that involves administering to the patient an effective amount of a composition containing peptide glutamyl-aspartyl-arginine of the formula H-Glu-Asp-Arg-OH as its active base.

4 Claims, 1 Drawing Sheet

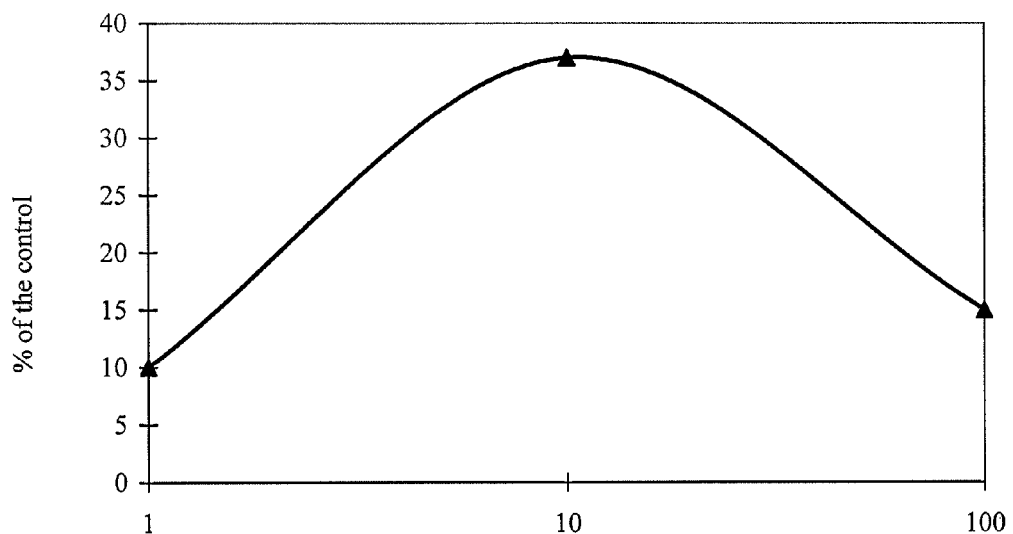
\* - P<0,05 as compared to the control taken as 100%.

```
                       SEQUENCE LISTING

<160> NUMBER OF SEQ ID NOS: 1

<210> SEQ ID NO 1
<211> LENGTH: 3
<212> TYPE: PRT
<213> ORGANISM: Artificial Sequence
<220> FEATURE:
<223> OTHER INFORMATION: Peptide compound H-Glu-Asp-Arg-OH stimulating
      central nervous system neurons regeneration by means of restoring
      the synthesis of tissue specific proteins, antioxidant effect,
      normalization of metabolism and bioelectric activity of neurons.

<400> SEQUENCE: 1

Glu Asp Arg
1
```

METHOD OF IMPROVING THE CONDITIONED REFLEX HABIT, THE MUSCLE TONUS, OR THE MOTION COORDINATION OF A PATIENT AFTER SUFFERING TRAUMA TO THE BRAIN CORTEX

CROSS-REFERENCE TO RELATED APPLICATIONS

This patent application is a continuation of copending U.S. patent application Ser. No. 12/298,420, filed Oct. 24, 2008, which is a national phase filing of PCT Patent Application No. PCT/RU2006/000653, filed on Dec. 4, 2006, which claims benefit to Russian Patent Application No. 2006118494, filed on May 30, 2006, the disclosures of which are incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 931 Byte ASCII (Text) file named "710881_ST25.TXT," created on Aug. 14, 2012.

BACKGROUND OF THE INVENTION

The invention is related to the medicinal means of treatment of diseases, traumas, as well as consequences of traumas of the central nervous system, and can be also used as a means of stimulating neurons regeneration.

There are known preparations effective on brain metabolism and integrative functions: Cerebrolysine, Pirazetam, Encephalolysade. Also there are preparations normalizing brain and system blood circulation: Stugeron, Cavinton; preparations for stopping psychopathologic manifestations: Meridyne, Amitriptyline; preparations effective on brain bioelectric activity: Phenobarbital, Convulex; countering liquorodynamic disorders: Veroshpiron, Furosemide (The Comprehensive Russian Encyclopaedia of Medicinal Means, Moscow, Remedium publishing house, V.2, 2002 (rus.)).

There is also known a synthetic peptide preparation stimulating functional activity of neurons (RU Patent No. 2155063, 1999).

Known medications exert only functional effects consisting in the improvement of metabolic processes in nervous system structures and the enhancement of its resistance to pathogenic influences.

It is necessary to note that no medications effective on the process of neurons regeneration were found in the prior art.

Presently there is an ever growing number of patients with different brain diseases, traumas, as well as consequences of central nervous system traumas, that is why the creation of new groups of preparations, including biologically active peptide substances, possessing the ability to regenerate neurons, is presently of significant importance.

BRIEF SUMMARY OF THE INVENTION

The claimed peptide has no structural analogues in the prior art.

The claimed invention has set and resolved the task of obtaining the new peptide, possessing biological activity, which manifests itself in the stimulation of neurons regeneration.

The technical result of the invention consists in the creation of a new peptide, stimulating neurons regeneration, as well as a pharmaceutical composition containing the new peptide as an active base, being used for stimulating neurons regeneration by restoring the synthesis of tissue specific proteins, as well as by means of its antioxidant effect and normalization of metabolism and bioelectric activity of neurons.

This invention is related to the peptide glutamyl-aspartyl-arginine with general formula H-Glu-Asp-Arg-OH sequence 1 [SEQ ID NO:1].

Peptide glutamyl-aspartyl-arginine with general formula H-Glu-Asp-Arg-OH sequence 1[SEQ ID NO:1] possesses the ability to stimulate the regeneration of neurons.

The other aspect of this invention is related to the pharmaceutical composition stimulating the regeneration of neurons, which contains the effective amount of peptide glutamyl-aspartyl-arginine with general formula H-Glu-Asp-Arg-OH sequence 1[SEQ ID NO:1] as its active base, as well as pharmaceutically acceptable carrier.

This pharmaceutical composition exists in the form, which is intended for parenteral administration.

The next aspect of this invention is related to the method of stimulating the regeneration of neurons, which consists in the administering to the patient of the pharmaceutical composition containing the effective amount of peptide glutamyl-aspartyl-arginine with general formula H-Glu-Asp-Arg-OH sequence 1[SEQ ID NO:1] as its active base, in the dose of 0.01-100 µg/kg of body weight, at least once a day throughout the period necessary for attaining therapeutic effect.

In this method the pharmaceutical composition is administered parenterally.

The peptide glutamyl-aspartyl-arginine with general formula H-Glu-Asp-Arg-OH is obtained using the classical method of peptide synthesis in solution.

The possibility of objective attaining of the technical result while using the claimed invention has been confirmed by reliable data indicated in the examples, containing the experimental data obtained in the studies performed in accordance with the methods traditional for this field.

The stimulating effect of peptide H-Glu-Asp-Arg-OH on the regeneration and integrative functions of neurons was identified in the peptide's experimental study. The study of the biological activity of the peptide was performed on brain cortex explants, in experimental models of traumatic damage of brain and spinal cord, hypoxia, and in patients with remote consequences of brain injury.

The notion "pharmaceutical composition" means such different medicinal forms containing the new peptide, which may be used in the medicine as a means of neuron regeneration stimulation.

To obtain pharmaceutical compositions covered by this invention, the effective amount of peptide H-Glu-Asp-Arg-OH as the active base (active substance) must be mixed with pharmaceutically acceptable carrier according to the methods of compounding, which are universally accepted in pharmaceutics.

The notion "effective amount" implies the use of such amount of the active base, which, according to its quantitative indices of activity and toxicity, as well as to the knowledge of a competent specialist, must be effective in the given medicinal form.

The carrier can have different forms, depending on the medicinal form of the substance, desirable for the administration to the organism.

For parenteral administration, the carrier is usually introduced into the physiological saline solution or sterile water, though other ingredients improving its stability or preserving sterility may also be added.

The subject matter of the claimed invention is explained by a FIGURE and tables.

Table 1 displays the effect of peptide H-Glu-Asp-Arg-OH on morphological and biochemical indices of guinea pig peripheral blood in the study of toxicity.

Table 2 displays the effect of peptide H-Glu-Asp-Arg-OH on the processes of peroxide lipid oxidation and peroxidation of proteins in rat brain cortex in hypoxia.

Table 3 displays the effect of peptide H-Glu-Asp-Arg-OH on the life span of isolated river crayfish neurons.

Table 4 displays the effect of peptide H-Glu-Asp-Arg-OH on the indices of corrective test performance by patients.

Table 5 displays the effect of peptide H-Glu-Asp-Arg-OH on the dynamics of EEG alpha index in patients.

BRIEF DESCRIPTION OF THE DRAWING

The FIGURE displays the effect of peptide H-Glu-Asp-Arg-OH on the development of brain cortex implants.

DETAILED DESCRIPTION OF EMBODIMENTS OF THE INVENTION

The invention is illustrated by an example of synthesis of peptide glutamyl-aspartyl-arginine with general formula H-Glu-Asp-Arg-OH (Example 1), by examples of studies of toxicity and biological activity of the peptide (Examples 2, 3, 4, 5, 6, 7), as well as by an example of the results of the peptide's clinical administration, displaying its pharmaceutical properties and confirming the possibility of attaining therapeutic effect (Example 8).

EXAMPLE 1

Synthesis of peptide H-Glu-Asp-Arg-OH

1. Product name: glutamyl-aspartyl-arginine.
2. Structural formula:

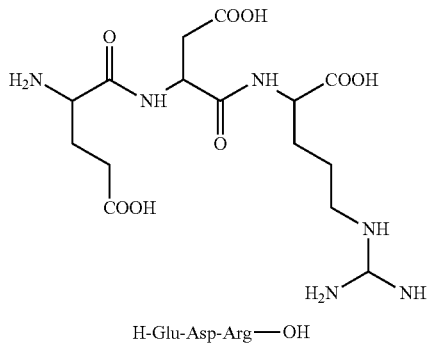

H-Glu-Asp-Arg—OH

3. Molecular formula without ion pair: $C_{15}H_{26}N_6O_8$.
4. Molecular weight without ion pair: 418.40.
5. Ion pair: acetate.
6. Appearance: white amorphous powder without smell.
7. Method of synthesis: the peptide is obtained by a classical method of synthesis in a solution by the following scheme:

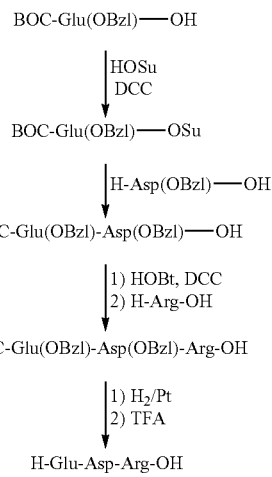

BOC—tert.butyloxycarbonyl group,
OSu—N-oxysuccinimide ester,
DCC—N,N'-dicyclohexylcarbodiimide,
OBzl—benzyl ester,
TFA—trifluoracetic acid,
HOBt—N-oxybenzotriazol,
Z—benzyloxycarbonyl group.

Properties of the finished product:
base substance content: 98.01% (by HPLC, 220 nm),
TLC—individual, $R_f$=0.65 (acetonitrile-water 1:3),
Moisture content: 6%,
pH of 0.01% solution: 4.88,
Specific rotary power: $[\alpha]_D^{22}$: −33° (c=1, $H_2O$), "Polamat A", Carl Zeiss Jena.

EXAMPLE OF SYNTHESIS

1) BOC-Glu(OBzl)-OSu, N-oxysuccinimide ester of N-tert.butyloxycarbonyl-(γ-benzyl)glutamic acid (I)

N-tert.butyloxycarbonyl-(γ-benzyl)glutamic acid BOC-Glu(OBzl)-OH (33.7 r, 0.1 mole) is dissolved in 50 ml of N,N'-dimethylformamide, cooled up to −10° C.; in the process of mixing cooled (4-6° C.) solutions of N,N'-dicyclohexylcarbodiimide (23.0 g, 0.11 mole) in 30 ml N,N'-dimethylformamide and N-hydroxysuccinimide (13.0 g, 0.11 mole) in 20 ml of N,N'-dimethylformamide. Reactive mixture is stirred for 12 hours, cooled with ice, and then for 24 hours at room temperature. The residue N,N'-dicyclohexylurea is filtered out, and the obtained solution of activated ester is used without extracting during the next stage.

2) BOC-Glu(OBzl)-Asp(OBzl)-OH, N-tert.butyloxycarbonile-(γ-benzyl)glutamyl-(βbenzyl)aspartate (II)

(β-benzyl)asparaginic acid H-Asp(OBzl)-OH (28.0 g, 0.12 mole) and 36 ml (0.12 mole) of triethylamine is suspended in 50 ml of N,N'-dimethylformamide and stirred for 1 hour. Then activated ester BOC-Glu(OBzl)-OSu (I) solution, obtained during the previous stage, is added in portions. The reactive mixture is stirred at room temperature for 48 hours. Then the mixture is acidified with 0.5 N sulphuric acid up to pH 2-3 and extracted with ethyl acetate 4×50 ml. The extracts are put together and subsequently washed by 0.5 N $H_2SO_4$ 3×50 ml, water 2×50 ml, 5% $NaHCO_3$ solution 2×50 ml, water 2×50 ml, saturated NaCl solution 2×50 ml. The organic layer is dried over $Na_2SO_4$, the solvent is removed in vacuo, the residue is crystallized under hexane. 50 g of product is obtained (92%). $R_f$=0.34 (benzene-acetone 2:1).

3) BOC-Glu(OBzl)-Asp(OBzl)-Arg-OH (III), N-tert-butyloxycarbonyl-(γ-benzyl)glutamyl-(β-benzyl) aspartyl arginine (III)

2.4 g (10 mmole) of arginine hydrochloride HCl H-Arg-OH is suspended in 10 ml of dimethylformamide and stirred for 24 hours. 2.4 g (4.4 mmole) of protected peptide (II) and 0.8 g (6 mmole) of oxybenzotriazol is separately dissolved in 10 ml of dimethylformamide and cooled up to −10° C. Then the solution of dicyclohexylcarbodiimide 1.25 g (6 mmole) cooled up to the same temperature is added in 5 ml of dimethylformamide. Activated ester is obtained during 20 minutes, then arginine suspension is added to the obtained reagent and stirred for 48 hours at room temperature. The fallout dicyclohexylurea is filtered out, the filtrate is acidified with 0.5 N sulphuric acid up to pH 3. Extraction is performed using 3×20 ml n-butyl spirit saturated with water. Extracts are put together and washed with water, organic solvent is removed in vacuo. The residue is crystallized under ester. Re-crystallization is performed from isopropyl spirit, after which the mixture is dried in vacuo over KOH.

800 mg of product are obtained (26%). $R_f$=0.87 (n-butanol-water-acetic acid 4:1:1).

4) H-Glu-Asp-Arg-OH (IV), glutamyl-aspartyl-arginine

Protected tripeptide BOC-Glu(OBz1)-Asp(OBz1)-Arg-OH (III) (0.80 g) is dissolved in the mixture of methyl spirit—water (4:1) and hydrated over catalyst Pd/C (5%) for 4 hours. Catalyst is filtered out, solvent is removed in vacuo, residue is dried in vacuo over KOH and $P_2O_5$. Then the product is dissolved in 2 ml of chlorous methylene-trifluoroacetic acid (5:1) mixture and held at room temperature for 2 hours. The fullness of deblockading reaction is controlled by TLC in acetonitrile-water system (1:3). Solvent is removed in vacuo, residue is dried in vacuo over KOH.

For the purpose of purification 300 mg of preparation is dissolved in 4 ml of 0.01% trifluoroacetic acid and subjected to highly productive liquid chromatography on reverse phase column 50×250 mm Diasorb-130-C16T, 7 μm. Chromatographer Beckman System Gold, 126 Solvent Module, 168 Diode Array Detector Module. Conditions of chromatography: A: 0.1% TFA; B: MeCN/0.1% TFA, gradient B 0→50% in 100 minutes. Sample volume 5 ml, detection at 215 nm, scanning 190-600 nm, flow rate 10 ml/min. Fraction is selected for 37.0-42.0 minutes. The solvent is removed in vacuo at the temperature not higher than 40° C., the removal is several times (5 times) repeated with 10 ml of 10% acetic acid solution. Finally the residue is dissolved in 20 ml of deionized water and lyophilized.

120 mg of purified substance in the form of amorphous white powder without smell is obtained.

5) Analysis of the Ready Substance

The base substance content is identified by HPLC on the column Phenomenex C 18 LUNA 4.6×150 mm. A: 0.1% TFA, B: MeCN; grad.B 0-100% in 10 min. Flow rate 1 ml/min. Detection at 220 nm, scanning 190-600 nm, sample 20 μl. Base substance content 98.01%.

TLC: individual, $R_f$=0.65 (acetonitrile-water 1:3, Sorbfil plates, silicagel 8-12 μm, developing chlorine/benzidine).

Moisture content: 6% (gravimetrically, judging by weight loss by drying of 20 mg at 100° C.).

pH of 0.01% solution: 4.88 (potentiometrically).

Specific rotary power: $[\alpha]_D^{22}$: −33° (c=1, $H_2O$), "Polamat A", Carl Zeiss Jena.

EXAMPLE 2

Study of Peptide H-Glu-Asp-Arg-OH Toxicity

Common toxicity of peptide H-Glu-Asp-Arg-OH was studied according to the requirements stated in the "Manual for experimental (pre-clinical) study of new pharmacological substances" (2000): acute toxicity in case of single administration of the substance and sub-acute and chronic toxicity in case of long-term administration of the peptide.

The study of acute toxicity was performed on 72 white mongrel male mice with body weight of 20-22 g. The animals were randomly subdivided into 6 equal groups. The substance was administered to the animals once, intramuscularly, in the doses of 1 mg/kg, 2 mg/kg, 3 mg/kg, 4 mg/kg, 5 mg/kg in 0.25 ml of sterile 0.9% NaCl solution. The control animals received 0.9% NaCl solution in the same volume.

The study of sub-acute toxicity was performed on 65 white mongrel male rats with body weight of 160-210 g. Experimental animals received the substance daily, intramuscularly for 90 days in the doses of 1 μg/kg, 0.1 mg/kg, 1 mg/kg in 0.5 ml of sterile 0.9% NaCl solution. Control animals received sterile 0.9% NaCl solution in the same volume. Morphology and properties of the animals' peripheral blood were studied before the administration of the substance, as well as on the $30^{th}$, $60^{th}$ and $90^{th}$ day after the beginning of the administration. Upon completion of the experiment biochemical and coagulologic indices of the blood were also evaluated.

The studies of chronic toxicity were conducted for 6 months, basing on the term of recommended clinical administration of the substance, on 84 male guinea pigs with body weight of 270-310 g. Experimental animals received the peptide daily, once a day, intramuscularly, for 6 months in the doses of 1 μg/kg, 0.1 mg/kg, 1 mg/kg in 0.5 ml of sterile 0.9% NaCl solution. Control animals received sterile 0.9% NaCl solution in the same volume and by the same schedule. Traditional methods were used for the evaluation of the following indices of the animals' peripheral blood: the quantity of erythrocytes, hemoglobin, reticulocytes, thrombocytes, leukocytes, leukocyte formula, erythrocyte sedimentation rate (ESR), erythrocyte resistance. Alongside with that, the content of total protein in the serum was identified using Lowry's method, as well as potassium and sodium content using the method of plasma spectrophotometry. After the completion of the experiment pathomorphologic studies of animal brain and spinal cord, spinal cord ganglia, thyroid gland, parathyroid glands, adrenal glands, testis, pituitary body, heart, lungs, aorta, liver, kidneys, urinary bladder, pancreas, stomach, small intestine, large intestine, thymus, spleen, lymph nodes and bone marrow were performed.

The study of acute toxicity showed, that a single administration of the studied peptide to animals in the dose exceeding the therapeutic one, which is recommended for clinical administration, by more than 5000 times, does not cause toxic reactions, which points out the width of diapason of possible therapeutic doses of the substance.

The study of subacute and chronic toxicity of the peptide showed the absence of any side effects in case of long-term administration of the substance in doses exceeding the therapeutic one by 100-1000 times. The study of peptide effect on guinea pig blood morphology and biochemical indices in 3 and 6 months after the beginning of the substance administration showed that no statistically significant changes in the studied indices took place (Table 1).

The evaluation of the animals' general status, of morphologic and biochemical indices of peripheral blood, of morphological status of the organs, of the status of cardiovascular and respiratory systems, as well as of liver and kidney functions revealed no pathologic alterations in the organism.

The absence of common toxicity allows to recommend the pharmaceutical composition, containing the peptide H-Glu-Asp-Arg-OH as its active base, for clinical studies.

EXAMPLE 3

Effect of Peptide H-Glu-Asp-Arg-OH on the Development of Brain Cortex Explants

This study was performed on 32 fragments of brain cortex from Wistar rats with body weight of 150-200 g. Nutritional medium for explants cultivation consisted of 35% Eagle's solution, 25% calf fetal serum, 35% Hank's solution, 5% chicken embryonic extract, with the addition of glucose (0.6%), insulin (0.5 units/ml), penicillin (100 units/ml), glutamine (2 mM). Brain cortex fragments were placed into this medium and cultivated in Petri dishes in the thermostat at the temperature of 36.7° C. for 48 hours. Peptide H-Glu-Asp-Arg-OH was added into the medium, reaching ultimate concentration of 1, 10 and 100 ng/ml.

Area index (AI), i.e. the ratio of total explant area together with the growth zone to the initial area of brain cortex fragment served as the criterion of biologic activity. The statistical significance of the difference between the compared mean AI values was evaluated using Student's t-criterion. AI values were expressed in percent, control AI values being considered as 100%.

The zone of control cortex explants growth consisted of short neurites, as well as outgoing glial cells and fibroblast-like cells.

The FIGURE displays the effect of peptide H-Glu-Asp-Arg-OH on the development of brain cortex explants.

It was found, that after 24 hours of cultivating the explants sprawled upon the collagen substrate, and proliferating and migrating cells began disseminating around the area of the explant. By the $3^{rd}$ day of the cultivation in case of peptide H-Glu-Asp-Arg-OH making 10 ng/ml a statistically significant AI growth by 37% was observed as compared to the control AI indices. The study of cortex explants after 7 days of cultivating revealed the same effects of neurites stimulation in case of the same concentrations. Sometimes statistically insignificant decrease in the AI of explants was observed, which is possibly due to the retraction of nerve fibers in case of prolonged cultivation terms.

The obtained results confirm the neurite stimulating activity of peptide H-Glu-Asp-Arg-OH.

EXAMPLE 4

Effect of Peptide H-Glu-Asp-Arg-OH on Reparative Processes in Rat Brain Cortex after Cranial Trauma The effect of peptide H-Glu-Asp-Arg-OH on reparative processes in the brain was estimated on the pattern of acute heavy cranial trauma. The dynamics of central nervous system functions restoration were identified by testing motion coordination and muscle tonus of the animals, as well as their ability to learning and reproducing the conditioned reflex habit.

24 white mongrel rats were subjected to heavy compression cranial trauma from a falling leaden bob. In 1, 12, 48 and 96 hours, the 15 experimental animals intramuscularly received peptide H-Glu-Asp-Arg-OH in the dose of 10 μg/kg in 0.5 ml of sterile 0.9% NaCl solution. The control animals received sterile physiological saline solution in the same volume and by the same schedule.

The estimation of the rats' ability to learn and reproduce the habits was performed using the test of conditioned active avoidance reflex (CAAR). Muscle tonus and motion coordination were tested by rotating the rats on a rod with increasing speed and measuring the time of their holding on to the rod.

In 48 hours after the trauma all surviving animals were unable to learn. In 96 hours after the trauma in the group of rats treated with peptide H-Glu-Asp-Arg-OH the number of animals capable of learning was 2 times larger, than in the control. In 30 days the indices of learning ability in rats treated with peptide H-Glu-Asp-Arg-OH were also higher than in the control.

Heavy cranial trauma caused a pronounced asthenic-neurotic syndrome and a decline of coordination and muscle tonus. The "rotating rod" test showed that peptide H-Glu-Asp-Arg-OH contributed to the regaining of motion coordination and muscle tonus in 48 hours after the trauma (the time of holding on to the rod was more than 2 times longer, than in the control).

Thus, the administration of peptide H-Glu-Asp-Arg-OH enabled a significant improvement in the animals' ability to learn and reproduce the conditioned reflex habit, as well as the normalization of the muscle tonus and motion coordination.

The ability of peptide H-Glu-Asp-Arg-OH to stimulate neuron regeneration was revealed already by the $5^{th}$ day after the trauma, and by the $14^{th}$ day the indices of the animals' learning ability were close to normal values.

Acute heavy cranial trauma entails the damage and death of brain gray substance neuron populations. Accelerated restoration of central nervous system functions in the early post-traumatic period under the effect of peptide H-Glu-Asp-Arg-OH confirms the peptide's ability to stimulate the reparative processes in the brain.

EXAMPLE 5

Effect of Peptide H-Glu-Asp-Arg-OH on Morphologic Alterations in the Central Nervous System of Rats in Case of Spinal Cord Trauma The study was performed on mature Wistar rats of both sexes with body weight of 180-200 g. The experimental group of 27 rats was subjected to spinal cord trauma.

The animals were injured in the lumbar segment of the spinal cord according to the following method. The lateral surfaces of anesthetized rats' vertebrae on the level of the last rib were compressed through the skin using dressing forceps with a force of 15 kg on the working surfaces. In 24 hours after the trauma the surviving animals were subdivided into 2 groups.

The animals of the first group received the peptide H-Glu-Asp-Arg-OH intramuscularly, daily, once a day in the dose of 10 μg/kg in 0.5 ml of sterile 0.9% NaCl solution, altogether for 10 days. The rats of the second group (control) received sterile physiological saline solution in the same volume.

Neurohistological studies were performed in the animals of both groups on the $30^{th}$ day of the experiment. For this purpose spinal cord ganglia were taken from the spots of injury and above the injured spots, as well as lumbar and cervical segments of the spinal cord and motor cortex fragments and pyramid tracts of the brain. Neurohistological studies were performed using electronic and luminous microscopy.

The samples intended for luminous microscopy were fixed in 96% spirit and 10% formalin, then packed into celloidin with subsequent staining with hematoxylin-eosine, as well as staining by Nissle, Van Gison, Weigert, Spielmeyer. The samples were fixed and cut in accordance with conventional methods of histological processing and staining of the samples.

The samples intended for electronic microscopy were fixed by 2% osmic acid with cacodylate buffer, then packed in Epon 812 and contrasted in lead nitrate by Reynolds. The preliminary evaluation of the samples was performed using semifine sections. Ultrafine sections were studied using electronic microscope UEM-100SKh.

All rats with spinal cord trauma displayed pathomorphologic alterations in neurons at the injury spot. These alterations were of different extent. Part of the neurons showed the axonal reaction. In this case the cells were swollen, and their contours were smoothened. Nissel's lumps looked as if they were reduced to dust-like fragments, with pale staining by main colors. Karyoplasms became bloomed, and nucleus was dislocated towards the periphery. A significant proportion of neurons were shrunken. In this case the cells were narrowed and protruded, with sharp angular contours. Lumps of chromatin were intensely stained, as was the nucleus. Nucleoles were hardly visible. Part of the nerve cells displayed ischemic alterations. Tigroid substance in their cytoplasm was significantly depleted, nucleus in such cells was hyperchromatic, slightly reduced in size, and in some cases the nucleus collapsed into separate lumps. Sometimes particles in the form of small intensely colored grains were observed on the periphery of the neurons, near the body and appendices (pericellular incrustation of Golgi networks). In the majority of cases there were neurons with edematous alterations. Nissel's substance in these neurons looked like a narrow coil on the periphery of the cytoplasm. The contours of cell bodies looked degraded. Cytoplasm melting spots in the form of shiny coils were identified around the nucleus. Some neurons were heavily altered. Cell bodies looked swollen, with uneven chromatolysis. Long segments of neuronal appendices were stained. Some cells looked as if they were "eaten up". They displayed uncolored spots in the form of vacuoles of different sizes and irregular shape. Less frequently neurons displayed hypertrophied glial elements, which pointed out the manifestations of neuronophagia. Nucleus lesion was characteristic for this type of alterations, with the nucleus being reduced in size, with noticeable hyperchromatosis, making the nucleoles almost indiscernible. Some neurons were altered in the form of drastic swelling. In this case cell bodies looked swollen. Nuclei were enlarged and diffusely colored. Cytoplasm showed small grainy objects homogenously colored light blue. In some zones of the lesion spot heavy destruction process was present in the form of scarce cellular elements, gaps between nerve cells, especially in the anterior "horns" of the spinal cord, where small gaps were rather common. In some spots, from which neurons had disappeared, glial tissue proliferation was observed. Nerve cells of posterior "horns" of the spinal cords were better preserved. Signs of diffusal demyelinization of nerve fibers were observed in the ventral segment of posterior spinal cord trunks and in anterior-lateral spinal cord trunks. Foci of spongiosity in the form of white substance edema were also present.

The above morphological situation was observed in rats of both experimental groups. However, control rats displayed much more cases of "heavy" and ischemic neuronal alterations, as compared to rats treated with peptide H-Glu-Asp-Arg-OH, having mainly "primarily irritated" cells in their spinal cords.

All animals showed active proliferation of astrocytic glia, especially of fibrosis astrocytes. Cells were misshapen, with picnoform nuclei and homogenized cytoplasm without outgrowths. The experimental animals displayed a more active oligodendroglial hyperplasia. Multiple edematous forms were found among its cells. Microglial elements were moderately proliferating, with manifestations of glial outgrowths fragmentation.

Cell alterations in the form of axon degeneration were observed in upper segments of the spinal cord and in the brain of control animals.

Electronic microscopy revealed radical alterations in the neurons, their outgrowths, glial elements and vessels in rats with spinal cord trauma. Neuronal cytoplasm showed reduced quantity of endoplasmatic network channels, swollen Golgi apparatus cisterns, a large number of fringy cavities, as well as small and large lysosomes. Dark mitochondrias with dense matrix without visible cristas was characteristic for the situation.

Nerve cells periphery displayed large dark lipids covered with stripes, as well as large vacuoles, i.e., multivesicular corpuscles formed, presumably, by swollen granular endoplasmic network channels deprived of ribosomes. Disintegration of chromatin, which formed strangely shaped agglomerations near the dense nuclear membrane, was identified in the nuclei of some neurons. Rats treated with peptide H-Glu-Asp-Arg-OH showed signs of restoration in the neuronal cells cytoplasm. Large quantities of free ribosomes and polyribosomes, as well as short profile cisterns of granular endoplasmatic cells were observed. The number of small Golgi cisterns without signs of swelling was increased. Cell periphery displayed only single transparent vacuoles and dark corpuscles.

All animals revealed significantly altered myelin fibers in the form of myelin fragmentation, distortion, compression of inner pivotal cylinders and, as a result, the presence of large bright spaces. Experimental rats showed restored homogeneity of certain myelin fibers.

Alterations of the synapses were represented by filamentous degeneration of post-synaptic formations. Experimental rats showed a significantly larger portion of normal (dendro-dendritic) synapses.

The upper spinal cord segments of experimental animals displayed similar alterations in nerve cells and their outgrowths. Neurons showed signs of functional tension. Cell cytoplasm had a large number of lysosomes, while in some mitochondrias no cristas were visible. Golgi apparatus looked moderately swollen. Karyóplasma was condensed due to excessively compact location of chromatin in the cell nuclei. Nerve fibers showed moderate myelin exfoliation and pivotal cylinders compression.

The above alterations were less pronounced in rats treated with H-Glu-Asp-Arg-OH peptide. Karyoplasma looked normal, with more regular Golgi cisterns. Endoplasmatic network channels formed large vacuoles, containing residues of waste organoids for their utilization. However, cell cytoplasm still revealed excess lysosomes, as well as swollen mitochondrias with randomly located cristas. Myelin fibers had a normal appearance in much more cases.

Thus, the administration of H-Glu-Asp-Arg-OH peptides to animals with spinal cord trauma produced a stimulating effect on spinal cord neurons regeneration.

EXAMPLE 6

Effect of Peptide H-Glu-Asp-Arg-OH on the Intensity of Free Radical Oxidation Reactions in Rat Brain Cortex in Case of Hypoxia The study was performed on 18 white mongrel rats. Peptide H-Glu-Asp-Arg-OH was administered to the animals intraperitoneally, in the dose of 1 µg in 1.0 ml of sterile physiological 0.9% NaCl solution once a day for 10 days. 24 hours after the completion of peptide administration the animals were subjected to hypoxic hypoxia. Hypoxia was modeled in the altitude chamber of flow-ejector type, the atmosphere pressure in the chamber being 0.029 MPa, which corresponds to the altitude of 9000 m above sea level. Compression and decompression rate made 0.005 MPa per minute. Carbon dioxide and moisture absorbent was present in the altitude chamber. The animals were held in the chamber for 3 hours in the conditions of free conduct and under constant observation.

The intensity of peroxide lipid oxidation (POL) was estimated judging by the level of initial POL products, i.e. diene conjugates, and terminal products, i.e. Schiff's bases, playing a significant role in neurons damage. The level of protein peroxidation was estimated by the level of carbonyl derivative amino acids in proteins after interaction with 2,4-dinitrophenylhydrazine.

It was found, that H-Glu-Asp-Arg-OH peptide suppressed POL products generation in the brain cortex. The peptide caused a statistically significant decrease in the level of diene conjugates, as well as a tendency towards a decrease in Schiff's bases content. The peptide also inhibited protein peroxidation alongside with POL (Table 2).

Data shows, that the administration of peptide H-Glu-Asp-Arg-OH to animals affected by hypoxia suppresses the generation of POL products and protein peroxidation in the brain cortex.

EXAMPLE 7

Effect of Peptide H-Glu-Asp-Arg-OH on the Life Span of Isolated Neurons of Crayfish *Astacus leptodactilus*

Isolated neurons of *Astacus leptodactilus* crayfish for the in vitro study of peptide H-Glu-Asp-Arg-OH on their life span were extracted by axotomia, being regarded as a model of cell death by apoptosis.

Stretching receptor neurons of a crayfish closely resemble central neurons of vertebrals by their electrophysiological, biological and structure properties. They generate spikes with nearly constant rate during 10-15 hours. Two symmetrical neurons (control and experimental) extracted from the abdominal segment were placed into 2 ml chambers filled with Harreveld's solution. Neuronal potentials were registered extracellularly on the axons by fastened glass pipette electrodes, then amplified and recorded using H-338 recorder. At the same time the frequency of action potentials was registered using two-channel analog frequency meter and H-339 data recorders. In the beginning of the experiment impulse frequency of experimental and control neurons was set on the level of 10-15 Hz by the stretching of the muscle. After 1 hour of stabile spike generation with constant rate peptide H-Glu-Asp-Arg-OH in the concentration of 10 µg/ml was added into the experimental chamber. The activity of the neurons was constantly recorded before the spontaneous termination of spikes generation. Life span of neurons was compared for each couple. Altogether 10 couples of neurons were used.

Spontaneous termination of isolated neuron impulse after 8-10 hours of comparatively stabile work with set frequency took place in the form of small several seconds long frequency fluctuations, after which slower rhythms with several minutes period appeared. Average frequency of action potentials was reduced, then certain impulses began falling out, pulsation became chaotic and soon faded.

The study revealed that H-Glu-Asp-Arg-OH peptide prolonged the life span of isolated neurons by 15%, in the average from 11.9 up to 13.7 hours (Table 3).

Delayed death of neurons under the effect of peptide H-Glu-Asp-Arg-OH confirms the neuroprotective effect of the peptide related to its influence on electrophysiological membrane processes and intracellular metabolism.

EXAMPLE 8

Efficacy of Peptide H-Glu-Asp-Arg-OH in Patients with Consequences of Cranial Trauma This study was performed on 25 patients aged 31-60 with remote consequences of cranial trauma, who were randomly subdivided into 2 groups. These patients sustained cranial traumas from 1 to 10 years ago. Main group patients were subdivided into 3 groups depending on the severity of their cranial trauma. Patients with the most severe consequences of cranial trauma received the pharmaceutical composition containing peptide H-Glu-Asp-Arg-OH once a day, intramuscularly, in the dose of 5.0 mg in 1 ml of sterile 0.9% NaCl solution for 10 days. Main group patients with cranial trauma consequences of intermediate severity were treated with the pharmaceutical composition containing peptide H-Glu-Asp-Arg-OH once a day, intramuscularly, in the dose of 10.0 µg in 1 ml of sterile 0.9% NaCl solution for 10 days. Main group patients with mild consequences of cranial trauma received the pharmaceutical composition containing peptide H-Glu-Asp-Arg-OH once a day, intramuscularly, in the dose of 1.0 µg in 1.0 ml of sterile 0.9% NaCl solution for 10 days.

Control patients received sterile 0.9% NaCl solution in the same volume and by the same schedule.

The administration of pharmaceutical composition containing the peptide H-Glu-Asp-Arg-OH caused good clinical results in 59.4% of the total number of patients, satisfactory results—in 31.9%, and no positive effect in 8.7% of patients. No negative effect of the pharmaceutical composition containing peptide H-Glu-Asp-Arg-OH on the status of any patient was registered. The patients reported memory improvement, lower intensity and duration of headaches, better emotional stability, as well as a sense of being rested after night sleep.

The efficacy of the pharmaceutical composition containing H-Glu-Asp-Arg-OH peptide was estimated judging by the effect on integral function of the brain, i.e., attention, and on bioelectric activity of the brain using the corrective test and electroencephalogram.

Patients from main groups, who were treated with pharmaceutical composition containing peptide H-Glu-Asp-Arg-OH in different doses, showed a statistically significant increase in the number of registered characters, as well as a decrease in the number of mistakes in the corrective test (Table 4).

Patients treated with the pharmaceutical composition containing peptide H-Glu-Asp-Arg-OH in different doses showed better results in the analysis of corrective test performance dynamics before and after treatment as compared to the control. This was manifested by the absence of sharp fluctuations in the number of registered signs during the same periods of time, as well as by the presence of "adaptation" period by the middle of the test and gradual decline of the curve by the end of the test, which points out better stability of attention in patients of main groups.

The evaluation of the effect of pharmaceutical composition containing peptide H-Glu-Asp-Arg-OH on bioelectric activity of the brain was performed by means of calculating the alpha index before and after the treatment. Most noticeable changes in the bioelectric activity of the brain were observed in patients of the main groups after the treatment with pharmaceutical composition containing peptide H-Glu-Asp-Arg-OH—a significant increase of alpha index took place as a result of the treatment (Table 5).

Thus, the data confirms the efficacy of pharmaceutical composition containing peptide H-Glu-Asp-Arg-OH as its active base on the integrative function of brain cells in patients with consequences of cranial trauma by means of neurons regeneration stimulation.

TABLE 1

Administration of peptide H-Glu-Asp-Arg-OH (1 μg/kg)

| Index | 3 months Control (n = 24) | 3 months Peptide (n = 24) | 6 months Control (n = 24) | 6 months Peptide (n = 24) |
|---|---|---|---|---|
| Erythrocytes, $\times 10^{12}$/l | 5.3 ± 0.6 | 5.4 ± 0.4 | 5.4 ± 0.3 | 5.3 ± 0.6 |
| Hemoglobin, g/l | 14.2 ± 1.4 | 14.3 ± 1.6 | 14.5 ± 1.3 | 14.5 ± 1.7 |
| Reticulocytes, % | 1.3 ± 0.07 | 1.3 ± 0.1 | 1.1 ± 0.05 | 1.2 ± 0.04 |
| Thrombocytes, $\times 10^9$/l | 143.7 ± 7.9 | 145.1 ± 7.8 | 144.5 ± 8.6 | 145.2 ± 8.3 |
| Leukocytes, $\times 10^9$/l | 9.4 ± 0.5 | 10.0 ± 0.5 | 9.6 ± 0.5 | 9.4 ± 0.8 |
| Stab neutrophils, % | 0.31 ± 0.04 | 0.32 ± 0.05 | 0.33 ± 0.04 | 0.34 ± 0.07 |
| Segmented neutrophils, % | 45.8 ± 2.1 | 46.4 ± 2.1 | 46.2 ± 3.5 | 44.7 ± 2.7 |
| Eosinophils, % | 0.69 ± 0.05 | 0.71 ± 0.06 | 0.72 ± 0.04 | 0.68 ± 0.05 |
| Basophils, % | 0.61 ± 0.04 | 0.65 ± 0.07 | 0.72 ± 0.03 | 0.67 ± 0.08 |
| Monocytes, % | 2.5 ± 0.02 | 2.4 ± 0.07 | 2.6 ± 0.06 | 2.4 ± 0.03 |
| Lymphocytes, % | 48.9 ± 2.5 | 51.4 ± 2.1 | 51.3 ± 2.7 | 50.5 ± 1.9 |
| ESR, mm/hour | 1.69 ± 0.05 | 2.07 ± 0.04 | 2.01 ± 0.05 | 1.88 ± 0.03 |
| Erythrocytes resistance, % NaCl | | | | |
| maximum | 0.41 ± 0.02 | 0.43 ± 0.06 | 0.42 ± 0.04 | 0.42 ± 0.03 |
| minimum | 0.32 ± 0.05 | 0.30 ± 0.01 | 0.34 ± 0.04 | 0.31 ± 0.05 |
| Total protein in the blood serum, g/l | 72.9 ± 3.1 | 71.4 ± 2.6 | 73.1 ± 3.4 | 72.6 ± 3.2 |
| Sodium in the blood serum, mmole/l | 153.9 ± 5.7 | 155.2 ± 5.9 | 155.5 ± 6.2 | 153.2 ± 7.4 |
| Potassium in the blood serum, mmole/l | 5.1 ± 2.3 | 5.1 ± 2.4 | 5.2 ± 2.1 | 5.3 ± 1.8 |

TABLE 2

| Index | Group of animals Control (hypoxia) | Group of animals Peptide H-Glu-Asp-Arg-OH + hypoxia |
|---|---|---|
| Diene conjugates (nmole/g of tissue) | 42.15 ± 2.35 | 28.57 ± 1.84* |
| Schiff's bases (conv. units/g of tissue) | 317.0 ± 24.7 | 255.4 ± 26.8 |
| Level of proteins peroxidation (μmole/mg of protein) | 9.69 ± 0.32 | 4.68 ± 0.07* |

*P < 0.01 as compared to the control.

TABLE 3

Life span of isolated crayfish neurons (hours)

| Control | Peptide H-Glu-Asp-Arg-OH |
|---|---|
| 11.9 ± 0.3 | 13.7 ± 0.2* |

*P < 0.05 as compared to the control.

TABLE 4

| Group of patients | Number of registered signs | Number of mistakes |
|---|---|---|
| Healthy | 2874.6 ± 93.4 | 2.7 ± 0.3 |
| Patients before treatment | 1519.1 ± 141.7 | 12.6 ± 1.3 |

TABLE 4-continued

| Group of patients | Number of registered signs | Number of mistakes |
|---|---|---|
| Patients after treatment with commonly used medications | 1967.5 ± 122.4* | 9.7 ± 1.2* |
| Patients of the main groups after treatment with peptide H-Glu-Asp-Arg-OH | 2429.6 ± 105.3*# | 6.4 ± 1.1*# |

*$P < 0.05$ as compared to the indices in patients before treatment.
$P < 0.05$ as compared to the indices in patients treated with commonly used medications.

TABLE 5

| Group of patients | Alpha index |
|---|---|
| Healthy | 52.9 ± 3.2 |
| Patients before treatment | 35.7 ± 4.6 |
| Patients after treatment with commonly used medications | 42.4 ± 2.8* |
| Patients of the main groups after treatment with peptide H-Glu-Asp-Arg-OH | 47.9 ± 3.1*# |

*$P < 0.01$ as compared to the indices in patients before treatment.
$P < 0.05$ as compared to the indices in patients treated with commonly used medications.

The invention claimed is:

1. A method of improving the conditioned reflex habit, the muscle tonus, or the motion coordination of a patient after suffering trauma to the brain cortex comprising administering to the patient an effective amount of a composition containing peptide glutamyl-aspartyl-arginine of the formula H-Glu-Asp-Arg-OH as its active base.

2. The method of claim 1, wherein the peptide is administered in the dose of 0.01-100 μg/kg of body weight of the patient.

3. The method of claim 1, wherein the peptide is administered parenterally.

4. The method of claim 3, wherein the peptide is administered intramuscularly.

* * * * *